United States Patent
Nagai et al.

(10) Patent No.: US 12,161,740 B2
(45) Date of Patent: Dec. 10, 2024

(54) COSMETIC PRODUCT

(71) Applicant: Shiseido Company, Ltd., Tokyo (JP)

(72) Inventors: Kouichi Nagai, Tokyo (JP); Kei Ujimoto, Tokyo (JP); Yuko Nagare, Tokyo (JP); Ryoya Ito, Tokyo (JP); Marianne Ayaka Touati, Tokyo (JP); Satoshi Yamaki, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 868 days.

(21) Appl. No.: 17/267,325

(22) PCT Filed: Aug. 9, 2019

(86) PCT No.: PCT/JP2019/031599
§ 371 (c)(1),
(2) Date: Feb. 9, 2021

(87) PCT Pub. No.: WO2020/032245
PCT Pub. Date: Feb. 13, 2020

(65) Prior Publication Data
US 2021/0338551 A1    Nov. 4, 2021

(30) Foreign Application Priority Data
Aug. 10, 2018   (JP) .................................. 2018-151677

(51) Int. Cl.
| A61K 8/35 | (2006.01) |
| A61K 8/86 | (2006.01) |
| A61Q 17/04 | (2006.01) |
| G01N 21/33 | (2006.01) |

(52) U.S. Cl.
CPC ................. *A61K 8/35* (2013.01); *A61K 8/86* (2013.01); *A61Q 17/04* (2013.01); *G01N 21/33* (2013.01); *A61K 2800/244* (2013.01)

(58) Field of Classification Search
None
See application file for complete search history.

(56) References Cited

U.S. PATENT DOCUMENTS

| 2009/0053153 A1 | 2/2009 | Lee et al. |
| 2014/0170192 A1 | 6/2014 | Halpern et al. |
| 2018/0289610 A1 | 10/2018 | Yamaki et al. |

FOREIGN PATENT DOCUMENTS

| CN | 101371816 A | 2/2009 |
| CN | 108289812 A | 7/2018 |
| EP | 2 933 628 A1 | 10/2015 |
| EP | 3 213 741 A1 | 9/2017 |
| EP | 3 261 607 A1 | 1/2018 |
| JP | 01-246216 A | 10/1989 |
| JP | 5184031 | * 10/2007 |
| JP | 2017-155048 A | 9/2017 |
| WO | WO-2008/006687 A1 | 1/2008 |
| WO | WO-2016/068300 A1 | 5/2016 |
| WO | WO-2017/057676 A1 | 4/2017 |

OTHER PUBLICATIONS

Cream SPF 50+ Mintel-cited on IDS.*
Cream SPF 50 , ID#3281253, Mintel GNPD, online, Sep. 2015, retrieved on Oct. 3, 2019, from URL: https://portal.mintel.com.
UV Protective Cream SPF 50+ PA++++, ID#5749529, Mintel GNPD, online, Jun. 2018, retrieved on Oct. 30, 2019, from URL: https://portal.mintel.com.
Whitening Essence Facial UV Sunscreen SPF 50+/PA++++, ID#4100943, Mintel GNPD, online, Jun. 2016, retrieved on Oct. 3, 2019, from URL: https://portal.mintel.com.
Database GNPD [Online] Mintel, "Cream SPF 50+," Shiseido, Sep. 8, 2015, Database accession No. 3281253, XP055903717, 4 pages.
Database GNPD [Online] Mintel, "UV Protective Cream SPF 50+ PA++++," Shiseido, Jun. 13, 2018, Database accession No. 5749529, XP055903725, 3 pages.
Database GNPD [Online] Mintel, "Whitening Essence Facial UV Sunscreen SPF 40+/PA++++," Shiseido, Jun. 27, 2016, Database accession No. 4100943, XP055903724, 3 pages.
Office Action dated Jul. 28, 2023 in CN 201980051724.X.

* cited by examiner

*Primary Examiner* — Danah Al-Awadi
(74) *Attorney, Agent, or Firm* — Foley & Lardner LLP

(57) ABSTRACT

The present invention relates to a cosmetic in which the ultraviolet protection effects are increased by heat, and a method for manufacture thereof. The manufacturing method of the present invention includes
(1) a step of preparing a sample composition containing (A) an ultraviolet protectant and (B) one or more humectants that have an IOB of 5.0 or lower and that are selected from among alkylene oxide derivatives and polyhydric alcohols; and
(2) a step of selecting a sample composition in which ultraviolet protection effects are increased after heat treatment in comparison to before heat treatment, in accordance with an evaluation method including the following steps (i) to (iv):
(i) a step of forming a coating film of the sample composition on a substrate,
(ii) a step of heat-treating the coating film of the sample composition,
(iii) a step of measuring ultraviolet protection effects of the coating film of the sample composition that has not been heat-treated and of the coating film of the sample composition that has been heat-treated, and
(iv) a step of comparing the measured ultraviolet protection effects.

6 Claims, 1 Drawing Sheet

[Fig. 1]
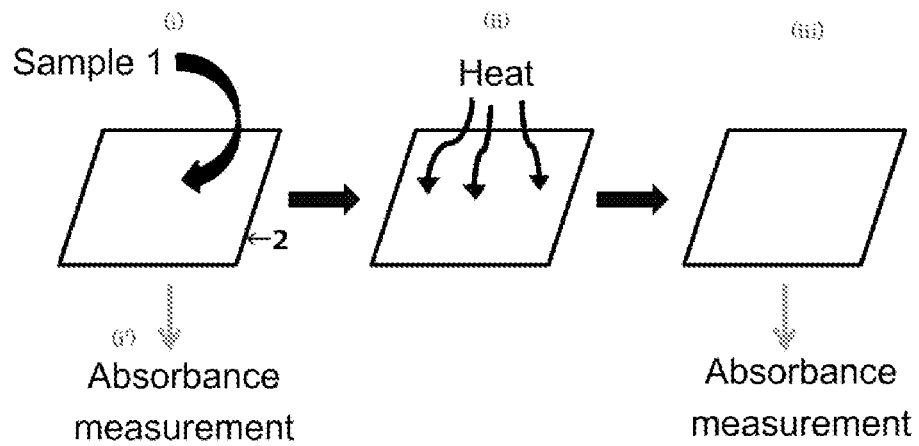
[Fig. 2]
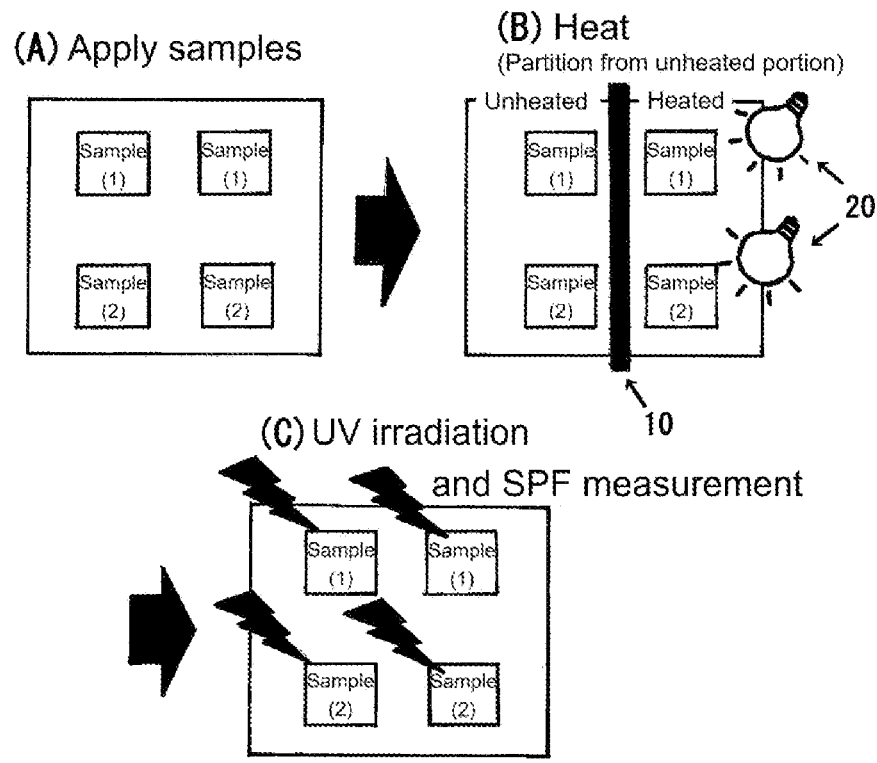

COSMETIC PRODUCT

CROSS-REFERENCE TO RELATED APPLICATIONS

This application is the U.S. National Stage of PCT/JP2019/031599, filed Aug. 9, 2019, which claims priority to JP 2018-151677, filed Aug. 10, 2018.

TECHNICAL FIELD

The present invention relates to a cosmetic having sunscreen effects and a manufacturing method thereof. More specifically, the present invention relates to a cosmetic having excellent heat resistance and having the unprecedented property in which heating increases the ultraviolet protection effects over those immediately after applying the cosmetic, and a method for manufacture thereof.

BACKGROUND ART

Cosmetics having sunscreen effects have the effects of reducing the amount of ultraviolet rays reaching the skin on which the cosmetics are applied and thereby suppressing the harmful impact thereof on the skin due to the action of ultraviolet absorbing agents or ultraviolet scattering agents blended into the cosmetics.

As an indicator of the ultraviolet protection effects of cosmetics, Sun Protection Factor (SPF) is the most widely known, representing the ultraviolet protection effects as an SPF value (for example, "SPF 30", etc.). In Japan, PFA (Protection Factor of UVA) or UVAPF (UVA Protection Factor of product) is used for ultraviolet rays in the UVA range, and the degree of UVA protection effects of a product is represented by PA (Protection grade of UVA) class ("PA++", etc.), which is based on the PFA or UVAPF value. In the United States, Critical Wavelength (CW), which indicates the balance of UVA and UVB protection effects, is used.

In recent years, in order to suppress the harmful impact of ultraviolet rays on the skin, cosmetics that provide high ultraviolet protection effects across a wide wavelength range from the UVA to the UVB ranges have come to be sought. For example, sunscreen products boasting SPF factors of 50 or higher (50+) and PA++++ have come onto the market.

The ultraviolet protection effects due to sunscreen products are obtained by the ultraviolet absorbing agents or ultraviolet scattering agents (titanium oxide, zinc oxide, etc.) that are blended in. However, ultraviolet absorbing agents include some in which the ultraviolet absorption performance is lowered by irradiation with light. The protection performance can also be lowered by the ultraviolet absorbing agents and ultraviolet scattering agents flowing away due to coming into contact with moisture.

Many improvements have been proposed for suppressing the photodegradation of ultraviolet protection effects (Patent Document 1), and regarding water resistance, a cosmetic having the innovative property in which contact with moisture does not decrease the ultraviolet protection effects but conversely increases the protection effects has been developed (Patent Document 2).

Meanwhile, as with light and moisture, decreases in ultraviolet protection effects due to heat cannot be ignored. In general, when a cosmetic that has been applied to skin is heated, the ultraviolet absorbing agents and other components contained in the cosmetic are degraded, thereby decreasing the ultraviolet protection effects. However, regarding heat, although there are examples in which the impact of heat, for example, on the emulsion stability of emulsion cosmetics including cosmetics have been considered (Patent Document 3), changes in the ultraviolet protection effects by heating have not been considered until now, and cosmetics having the purpose of suppressing decreases in ultraviolet protection effects due to heat have not previously been proposed.

RELATED ART

Patent Documents

Patent Document 1: JP 2010-150172 A
Patent Document 2: WO 2016/068300
Patent Document 3: JP 4397286 B

SUMMARY OF THE INVENTION

Problem to be Solved by the Invention

An objective of the present invention is to provide a cosmetic having the innovative, unprecedented property in which the ultraviolet protection effects do not decrease, but conversely increase, due to heat.

Thus, a problem addressed by the present invention is to provide a cosmetic in which the ultraviolet protection effects are increased by heat, and a method for manufacture thereof.

Means for Solving the Problem

As a result of performing diligent research towards solving the above-mentioned problem, the present inventors discovered that a cosmetic containing (A) an ultraviolet protectant and (B) a specific humectant, and further selected by a prescribed evaluation method, has ultraviolet protection effects that, rather than being degraded, conversely increase when heat is applied during actual use, thereby completing the present invention.

In other words, one embodiment of the present invention provides a manufacturing method for a cosmetic in which ultraviolet protection effects are increased by heat, the method including
(1) a step of preparing a sample composition containing
  (A) an ultraviolet protectant and (B) one or more humectants that have an IOB of 5.0 or lower and that are selected from among alkylene oxide derivatives and polyhydric alcohols; and
(2) a step of selecting a sample composition in which ultraviolet protection effects are increased after heat treatment in comparison to before heat treatment, in accordance with an evaluation method including the following steps (i) to (iv):
  (i) a step of forming a coating film of the sample composition on a substrate,
  (ii) a step of heat-treating the coating film of the sample composition,
  (iii) a step of measuring ultraviolet protection effects of the coating film of the sample composition that has not been heat-treated and of the coating film of the sample composition that has been heat-treated, and
  (iv) a step of comparing the measured ultraviolet protection effects.

Another embodiment of the present invention provides a cosmetic manufactured by a method including
(1) a step of preparing a sample composition containing
  (A) an ultraviolet protectant and (B) one or more humectants that have an IOB of 5.0 or lower and that are selected from among alkylene oxide derivatives and polyhydric alcohols; and (2) a step of selecting a sample composition in which ultraviolet protection effects are increased after heat treatment in comparison to before heat treatment, in accordance with an evaluation method including the following steps (i) to (iv):

(i) a step of forming a coating film of the sample composition on a substrate, (ii) a step of heat-treating the coating film of the sample composition, (iii) a step of measuring ultraviolet protection effects of the coating film of the sample composition that has not been heat-treated and of the coating film of the sample composition that has been heat-treated, and (iv) a step of comparing the measured ultraviolet protection effects.

Yet another embodiment of the present invention provides a cosmetic containing (A) an ultraviolet protectant and (B) one or more humectants that have an IOB of 5.0 or lower and that are selected from among alkylene oxide derivatives and polyhydric alcohols, wherein an absorbance of a coating film increases after being heated.

Effects of the Invention

With the cosmetic of the present invention, the ultraviolet protection effects significantly increase after heat has been applied in comparison to those immediately after the cosmetic has been applied to the skin. In other words, the cosmetic according to the present invention is an innovative cosmetic having the property, contrary to conventional expectations, in which heat, which had been considered to cause degradation of the effects in conventional cosmetics, conversely increases the ultraviolet protection effects.

BRIEF DESCRIPTION OF THE DRAWINGS

FIG. 1 is an explanatory diagram schematically indicating the evaluation method in the present invention.

FIG. 2 is an explanatory diagram schematically indicating an example of the evaluation method in the present invention, which is suitable for implementation in vivo.

MODES FOR CARRYING OUT THE INVENTION

1. Cosmetic Manufacturing Method

The manufacturing method of the cosmetic according to the present invention is divided into (1) a step for preparing a sample composition, and (2) a step for selecting a sample composition.

In the present specification, a "sample composition" is a concept that simply refers to a composition containing (A) an ultraviolet protectant and (B) a humectant, including those in which the ultraviolet protection effects after heat treatment do not increase in comparison to those before heat treatment. On the other hand, the "cosmetic" according to the present invention refers to a sample composition that has been selected as having ultraviolet protection effects that increase after heat treatment.

Hereinafter, the features of the present invention will be successively explained in detail.

(1) Step for Preparing Sample Composition

In this step, a sample composition is prepared by blending at least (A) an ultraviolet absorbing agent and (B) a humectant.

< (A) Ultraviolet protectant (ultraviolet absorbing agent and/or ultraviolet scattering agent)>

The (A) ultraviolet protectant (hereinafter sometimes referred to simply as "component (A)") blended into the sample composition refers to an ultraviolet absorbing agent and/or an ultraviolet scattering agent, and a type that is normally blended into cosmetics may be used.

The ultraviolet absorbing agent is not particularly limited, and a wide range of ultraviolet absorbing agents that are generally used in cosmetics can be named. Examples include benzoic acid derivatives, salicylic acid derivatives, cinnamic acid derivatives, dibenzoyl methane derivatives, $\beta,\beta$-diphenyl acrylate derivatives, benzophenone derivatives, benzylidene camphor derivatives, phenylbenzimidazole derivatives, triazine derivatives, phenylbenzotriazole derivatives, anthranil derivatives, imidazoline derivatives, benzalmalonate derivatives, 4,4-diaryl butadiene derivatives and the like. Hereinafter, specific examples and product names will be mentioned, but there is no limitation thereto.

Examples of benzoic acid derivatives include ethyl para-aminobenzoate (PABA), ethyl-dihydroxypropyl PABA, ethylhexyl-dimethyl PABA (e.g. "Escalol 507": ISP), glyceryl PABA, PEG-25-PABA (e.g. "Uvinul P25": BASF), diethylamino hydroxybenzoyl hexyl benzoate (e.g. "Uvinul A Plus") and the like.

Examples of salicylic acid derivatives include homosalate ("Eusolex HMS": Rona/EM Industries), ethylhexyl salicylate (e.g. "Neo Heliopan OS": Haarmann & Reimer), dipropylene glycol salicylate (e.g. "Dipsal": Scher), TEA salicylate (e.g. "Neo Heliopan TS": Haarmann & Reimer) and the like.

Examples of cinnamic acid derivatives include octyl methoxycinnamate or ethylhexyl methoxycinnamate (e.g. "Parsol MCX": Hoffman-La Roche), isopropyl methoxycinnamate, isoamyl methoxycinnamate (e.g. "Neo Heliopan E1000": Haarmaan & Reimer), cinnoxate, DEA methoxycinnamate, diisopropyl methyl cinnamate, glyceryl ethylhexanoate dimethoxycinnamate, di-(2-ethylhexyl)-4'-methoxybenzalmalonate and the like.

Examples of dibenzoyl methane derivatives include 4-tert-butyl-4'-methoxy dibenzoyl methane (e.g. "Parsol 1789") and the like.

Examples of $\beta,\beta$-diphenyl acrylate derivatives include octocrylene (e.g. "Uvinul N539T": BASF) and the like.

Examples of benzophenone derivatives include benzophenone-1 (e.g. "Uvinul 400": BASF), benzophenone-2 (e.g. "Uvinul D50": BASF), benzophenone-3 or oxybenzone (e.g. "Uvinul M40": BASF), benzophenone-4 (e.g. "Uvinul MS40": BASF), benzophenone-5, benzophenone-6 (e.g. "Helisorb 11": Norquay), benzophenone-8 (e.g. "Spectra-Sorb UV-24": American Cyanamid), benzophenone-9 (e.g. "Uvinul DS-49": BASF), benzophenone-12 and the like.

Examples of benzylidene camphor derivatives include 3-benzylidene camphor (e.g. "Mexoryl SD": Chimex), 4-methylbenzylidene camphor, benzylidene camphor sulfonic acid (e.g., "Mexoryl SL": Chimex), camphor benzalkonium methosulfate (e.g. "Mexoryl SO": Chimex), terephthalylidene dicamphor sulfonic acid (e.g. "Mexoryl SX": Chimex), polyacrylamide methylbenzylidene camphor (e.g. "Mexoryl SW": Chimex) and the like.

Examples of phenylbenzimidazole derivatives include phenylbenzimidazole sulfonic acid (e.g. "Eusolex 232": Merck), disodium phenyldibenzimidazole tetrasulfonate (e.g. "Neo Heliopan AP": Haarmann & Reimer) and the like.

Examples of triazine derivatives include bis-ethylhexyloxyphenol methoxyphenyl triazine (e.g. "Tinosorb S": Ciba Specialty Chemicals), ethylhexyl triazone (e.g. "Uvinul T150": BASF), diethylhexyl butamido triazone (e.g. "Uvasorb HEB": Sigma 3V), 2,4,6-tris (diisobutyl-4'-aminobenzalmalonate)-s-triazine, 2,4,6-tris [4-(2-ethylhexyloxycarbonyl) anilino]-1,3,5-triazine and the like.

Examples of phenylbenzotriazole derivatives include drometrizole trisiloxane (e.g. "Silatrizole": Rhodia Chimie), methylene bis (benzotriazolyl tetramethylbutyl phenol) (e.g. "Tinosorb M" (Ciba Specialty Chemicals)) and the like.

Examples of anthranil derivatives include menthyl anthranilate (e.g. "Neo Heliopan MA": Haarmann & Reimer) and the like.

Examples of imidazoline derivatives include ethylhexyl dimethoxy benzylidene dioxoimidazoline propionate and the like.

Examples of benzalmalonate derivatives include polyorganosiloxanes having benzalmalonate functional groups (e.g. Polysilicone-15: "Parsol SLX": DSM Nutrition Japan) and the like.

Examples of 4,4-diarylbutadiene derivatives include 1,1-dicarboxy (2,2'-dimethylpropyl)-4,4-diphenylbutadiene and the like.

Particularly preferred examples include, but are not limited to, organic ultraviolet absorbing agents such as ethylhexyl methoxycinnamate, octocrylene, dimethicodiethyl benzalmalonate, polysilicone-15, 4-tert-butyl-4'-methoxy dibenzoyl methane (t-butyl methoxy dibenzoyl methane), ethylhexyl triazone, diethylamino hydroxy benzoyl hexyl benzoate, bis-ethylhexyloxyphenol methoxyphenyl triazine, oxybenzone-3, methylene bis-benzotriazolyl tetramethylbutyl phenol, phenylbenzimidazole sulfonic acid, 3-(4'-methylbenzylidene)-d,l-camphor, 3-benzylidene-d,l-camphor, homosalate and ethylhexyl salicylate.

However, when 4-tert-butyl-4'-methoxy dibenzoyl methane is blended, the blended amount thereof should preferably be small. For example, the amount should preferably be less than 0.5% by mass relative to the total amount of the cosmetic, or 10% by mass or less relative to the total amount of component (A). This is because 4-tert-butyl-4'-methoxy dibenzoyl methane has a tendency to hinder the increase in ultraviolet protection effects due to heating when the (B) humectant is blended, thus making it difficult to actually experience a boost in the ultraviolet protection effects due to heat.

The ultraviolet scattering agent used in the present invention is not particularly limited, but specific examples include fine-particle metal oxides such as, for example, zinc oxide, titanium oxide, iron oxide, cerium oxide and tungsten oxide.

The ultraviolet scattering agent may be non-surface-treated or may be treated with various types of hydrophobic surface treatments, but those that are hydrophobically surface-treated are preferably used. As the surface treatment agent, it is possible to use a type that is commonly used in the cosmetics field including, for example, a silicone such as dimethicone and alkyl-modified silicone, an alkoxysilane such as octyltriethoxysilane, a dextrin fatty acid ester such as dextrin palmitate, or a fatty acid such as stearic acid.

The (A) ultraviolet protectant in the present invention includes embodiments consisting only of an ultraviolet absorbing agent, embodiments consisting only of an ultraviolet scattering agent, and embodiments including both an ultraviolet absorbing agent and an ultraviolet scattering agent.

Although the blended amount of the (A) ultraviolet protectant is not particularly limited, the amount should normally be at least 5% by mass, for example, 5% to 40% by mass, preferably 6% to 40% by mass, and more preferably 7% to 30% by mass relative to the total amount of the sample composition. If the blended amount of the (A) ultraviolet protectant is less than 5% by mass, then sufficient ultraviolet protection effects are difficult to obtain, and even if more than 40% by mass is blended, an increase in the ultraviolet protection effects commensurate with the blended amount cannot be expected, and the stability is worsened.

< (B) Humectant>

The (B) humectant (hereinafter sometimes referred to simply as "component (B)") blended in the sample composition has an IOB of 5.0 or lower, more preferably 3.0 or lower, and even more preferably 2.5 or lower. If the IOB value exceeds 5.0, then there are cases in which ultraviolet protection performance increase effects due to heat cannot be sufficiently obtained. The lower limit of the IOB value is not particularly limited (0 or higher, for example, 0.0001 or higher, 0.001 or higher, or 0.01 or higher, etc.).

"IOB" is an abbreviation for "Inorganic/Organic Balance", specifically defined as IOB value=inorganic value/organic value. The organic value and the inorganic value are characteristic values set for various types of atoms or functional groups in the Organic Conceptual Diagram. The Organic Conceptual Diagram is widely used, particularly in the environmental chemistry field and the pharmacochemistry field, as well-expressing the properties of organic substances having relatively complex interactions. For details, see, for example, Yoshio Koda, "Yuki Gainenzu-Kiso to Oyo-" [Organic Conceptual Diagram-Fundamentals and Applications], pp. 11-17, Sankyo Shuppan, 1984).

Among these humectants, in particular, one or more types selected from among alkylene oxide derivatives and polyhydric alcohols can be favorably used.

Examples of alkylene oxide derivatives include the polyoxyalkylene/polyoxyethylene copolymer dialkyl ethers represented by the following formula (I):

$$R_1O\text{-}[(AO)_m(EO)_n]\text{-}R^2 \qquad (I)$$

In the above formula (I), AO denotes an oxyalkylene group having 3 to 4 carbon atoms. Specific examples include an oxypropylene group, an oxybutylene group, an oxyisobutylene group, an oxytrimethylene group and an oxytetramethylene group, among which an oxypropylene group and an oxy butylene group are preferred. EO represents an oxyethylene group.

The symbol m represents the average number of moles of AO added, such that $1 \leq m \leq 70$, preferably $1 \leq m \leq 30$, and more preferably $1 \leq m \leq 20$. The symbol n represents the average number of moles of EO added, such that $1 \leq n \leq 70$, preferably $1 \leq n \leq 30$, and more preferably $1 \leq n \leq 20$. Additionally, m+n is 40 or less, preferably 25 or less, and more preferably 20 or less.

The order of addition of AO and EO is not particularly limited. AO and EO may be added in the form of blocks so as to form a block copolymer, or may be randomly added so as to form a random copolymer. Block copolymers include not only copolymers with two blocks, but also those having three or more blocks. Preferably, a random copolymer is used.

The molecular weight of the polyoxy alkylene/polyoxyethylene copolymer dialkyl ether represented by formula (I)

should be 100 to 10000, preferably 200 to 5000, and more preferably 300 to 2000. The ratio [EO/(AO+EO)] of the amount of EO to the total amount of AO and EO in each molecule is preferably 20% to 80% by mass.

$R_1$ and $R_2$, each independently, represent a hydrogen atom or a hydrocarbon group having one to four carbon atoms. Examples of hydrocarbon groups include methyl groups, ethyl groups, n-propyl groups, isopropyl groups, n-butyl groups, sec-butyl groups and tert-butyl groups. Methyl groups and ethyl groups are preferred.

The $R_1$ and $R_2$ in each molecule may be the same type of hydrocarbon group, a mixture of a hydrocarbon group and a hydrogen atom, or a mixture of multiple hydrocarbon groups having different numbers of carbon atoms. However, for each of $R_1$ and $R_2$, the ratio between the numbers of hydrocarbon groups and hydrogen atoms that are present should be such that the ratio (Y/X) of the number (Y) of hydrogen atoms to the number (X) of hydrocarbon groups is preferably 0.15 or lower, and more preferably 0.06 or lower.

Specific examples of polyoxy alkylene/polyoxyethylene copolymer dialkyl ethers that can be favorably used in the present invention include, but are not limited to, the following polyoxypropylene/polyoxyethylene copolymer dimethyl ethers:

PEG/PPG-9/2 dimethyl ether
PEG/PPG-17/4 dimethyl ether
PEG/PPG-14/7 dimethyl ether
PEG/PPG-11/9 dimethyl ether
PEG/PPG-55/28 dimethyl ether
PEG/PPG-36/41 dimethyl ether
PEG/PPG-6/3 dimethyl ether
PEG/PPG-8/4 dimethyl ether
PEG/PPG-6/11 dimethyl ether
PEG/PPG-14/27 dimethyl ether Alkylene oxide derivatives tend to have better ultraviolet protection performance increase effects due to heat as the molecular weight becomes relatively smaller. Therefore, among the polyoxypropylene/polyoxyethylene copolymer dimethyl ethers listed above, PEG/PPG-9/2 dimethyl ether exhibits the strongest effects.

Meanwhile, examples of polyhydric alcohols include the polyalkylene glycols of formula (II) below, as well as butylene glycol, dipropylene glycol, diglycerin, propanediol, erythritol, xylitol, methylglyceth-10, sorbitol and the like.

In this case, the polyalkylene glycol is represented by the following formula (II):

$$HO(RO)_pH \qquad (II)$$

In the above formula, RO denotes an oxyalkylene group having two to four carbon atoms, and p is 3 to 500.

Specifically, it is selected from among those usable in skin preparations for external use, such as cosmetics, and includes polyethylene glycol (also represented by "PEG"), polypropylene glycol (also represented by "PPG") and polybutylene glycol (also represented by "PBG") and the like.

Among the above, polyethylene glycols in which, in formula (II) above, RO is an oxyethylene group, and p is in the range 3 to 500, more preferably 3 to 60, are preferred. The preferred average molecular weight of the polyethylene glycol is within the range 150 to 23000, more preferably 150 to 3000. Specific examples include polyethylene glycol 300, polyethylene glycol 400, polyethylene glycol 1500, polyethylene glycol 20000 and the like.

Polyalkylene glycols tend to have better ultraviolet protection performance increase effects due to heat as the molecular weight becomes relatively smaller. Therefore, among the polyethylene glycols listed above, particularly strong effects are obtained when polyethylene glycol 300 or polyethylene glycol 400 is used.

The (B) humectant in the present invention includes embodiments consisting only of an alkylene oxide derivative, embodiments consisting only of a polyhydric alcohol, and embodiments including both an alkylene oxide derivative and a polyhydric alcohol. Among these, those including at least one each of an alkylene oxide derivative and a polyhydric alcohol are preferable. In particular, the ultraviolet protection effects due to heat become prominent when a low-molecular-weight polyoxypropylene/polyoxyethylene copolymer dimethyl ether and a low-molecular-weight polyhydric alcohol are contained in combination. Specific examples of such combinations include, in particular, a combination of PEG/PPG-9/2 dimethyl ether and polyethylene glycol 300.

The blended amount of the (B) humectant should be at least 0.1% by mass or more, for example, 0.1% to 25% by mass, preferably 1.0% to 20% by mass relative to the total amount of the sample composition. If the blended amount is less than 0.1% by mass, then there are cases in which ultraviolet protection performance increase effects due to heat cannot be sufficiently obtained. On the other hand, if the blended amount of the (B) humectant is too large, then there are cases in which the stability and the texture are affected.

<Optional Blended Components>

Aside from the above-mentioned component (A) and component (B), components that are normally used in cosmetics may be blended into the sample composition within a range not compromising the effects of the present invention. For example, it is possible to appropriately blend, as needed, pH adjusters, chelating agents, preservatives, antioxidants, oil-based active agents, surfactants, water phase thickeners, alcohols, powder components, colorants, pigments, medicinal agents and the like. Examples of medicinal agents include ascorbic acid (vitamin C), tranexamic acid, kojic acid, ellagic acid, albutin, alkoxysalicylic acid, nicotinic acid amide, glycyrrhizinic acid, tocopherol, retinol, and salts or derivatives of the above (e.g., sodium L-ascorbate, L-ascorbic acid ester magnesium salts, L-ascorbic acid glucoside, 2-O-ethyl-L-ascorbic acid, 3-O-ethyl-L-ascorbic acid, 4-methoxysalicylic acid sodium salts, 4-methoxysalicylic acid potassium salts, dipotassium glycyrrhizinate, stearyl glycyrrhizinate, tocopherol acetate, retinol acetate and retinol palmitate). Additionally, humectants having an IOB value higher than 5, such as glycerin, may also be blended within a range not inhibiting the effects of the present invention.

Additionally, it is preferable for at least 5% by mass of an alcohol to be contained relative to the total amount of the sample composition. By blending at least 5% by mass of an alcohol, a silky texture and increased spreadability can be expected. However, if the blended amount of the alcohol is too large, then there are cases in which the stability becomes worse. Therefore, the amount should preferably be not more than 30% by mass relative to the total amount of the sample composition.

Additionally, it is preferable for a spherical powder to be further contained. By blending in a spherical powder, stickiness is suppressed, the texture is improved, and a good, silky touch can be obtained. The spherical resin powder may be arbitrarily used without any particular restrictions, as long as it is of a type that is used in cosmetic products or the like in general. Examples include (meth)acrylic acid ester resin powders, polyamide resin powders (nylon powders), polyethylene powders, polystyrene powders, styrene/(meth)

acrylic acid copolymer resin powders, benzoguanamine resin powders, polytetrafluoroethylene powders, cellulose powders, trimethyl silsesquioxane powders and the like, as well as organopolysiloxane elastomer spherical powders or composite spherical powders having the above as base powders. The average particle size of the spherical powder should preferably be 3 to 20 μm. If the size is smaller than 3 μm, then the effect of suppressing stickiness is not observed, and if the size is larger than 20 μm, then there are cases in which graininess is conversely felt. The blended amount of the spherical powder is not particularly limited, but should preferably be 1% to 30% by mass, and more preferably 3% to 20% by mass.

Furthermore, in the case that the sample composition is an emulsion, then an ester oil having an IOB value of 0.3 or higher should preferably be blended in the oil phase thereof.

(2) Step for Selecting Sample Composition

In this step, the impact of heat on the ultraviolet protection effects is investigated for the sample compositions obtained as described above, by means of the evaluation method described below, to select a sample composition (the "cosmetic" in the present invention) in which the ultraviolet protection effects are increased by heat.

The evaluation method used in the present invention includes the following steps (i) to (iv):
(i) a step of forming a coating film of the sample composition on a substrate,
(ii) a step of heat-treating the coating film of the sample composition,
(iii) a step of measuring ultraviolet protection effects of the coating film of the sample composition that has not been heat-treated and of the coating film of the sample composition that has been heat-treated, and
(iv) a step of comparing the measured ultraviolet protection effects.

This evaluation method will be explained in detail below with reference to the drawings.

FIG. 1 is a diagram for schematically explaining the evaluation method in the present invention.

In step (i), a prescribed amount of a sample (sample composition) 1 of the cosmetic is applied to a substrate 2 and optionally dried, thereby forming a coating film of the sample 1 on the substrate 2. A step (i') for measuring the ultraviolet protection effects (such as absorbance) before heating the sample coating film that has been formed may be optionally included.

In the next step (ii), heat is applied to the sample coating film formed in step (i). This heating step (ii) may involve applying heat after forming the sample coating on the substrate, or may involve heating the substrate in step (i) to a prescribed temperature beforehand, so that the sample is heated by being applied (in other words, step (i) and step (ii) are implemented at the same time).

Next, in step (iii), the ultraviolet protection effects (such as the absorbance) of the sample coating film that has been heat-treated are measured.

In the evaluation method of the present invention, another sample (second sample) of the same cosmetic as the above-described sample may be prepared, the second sample may be applied to a different area of the substrate in the aforementioned step (i) and optionally dried, thereby forming a second sample coating film (step (iA)), the second sample coating film may be held (step (iiA)), preferably at ambient temperature, without being subjected to the heat treatment (step (ii)), and step (iii) may include a step (step (iiiA)) for measuring the ultraviolet protection effects of the unheated second sample coating film.

Finally, in step (iv), the ultraviolet protection effects of the heated sample coating film are compared with the ultraviolet protection effects of the unheated second sample coating film (not illustrated).

Specifically, in step (i), when measuring the ultraviolet protection effects of the sample coating film before heating (step (i')), the ultraviolet protection effects before being heated are compared (step (iv')) with the ultraviolet protection effects after heating, measured in step (iii).

On the other hand, in the case in which the second sample coating film is formed in step (i) (step (iA)), the ultraviolet protection effects of the unheated second sample coating film (iiiA)) are compared (step (iv'A) with the ultraviolet protection effects after heating, measured in step (iii).

The evaluation method of the present invention may be implemented in vivo or in vitro. These shall be explained below.

(A) In Vivo Evaluation Method

FIG. 2 is a diagram for explaining one example of the evaluation method of the present invention that is implemented in vivo.

Below is an example of the case in which SPF measurement is employed as the ultraviolet protection effect measurement. Regarding the details of the SPF measurement method, see "Japanese Cosmetic Industry Association SPF Measurement Standards (revised 2011)" and "ISO 24444 Cosmetics-Sun protection test methods—In vivo determination of the sun protection factor (SPF)".

First, a sample (sample composition) of the cosmetic is applied to a prescribed portion of a substrate (the skin of a test subject) and optionally dried to form a sample coating film (FIG. 2 (A)). At that time, coating films of the same sample should preferably be formed by being applied to at least two locations on the substrate. In FIG. 2, two types of samples, i.e., sample (1) and sample (2), are applied at two locations.

Although the prescribed area is not particularly limited, it should preferably be an area on the back of the test subject between the scapulae and the waist.

Next, as illustrated in FIG. 2 (B), at least one of the sample coating films formed on the at least two locations on the substrate is subjected to heat treatment in which heat is applied.

Before heat treatment, measures should preferably be taken to keep the heat from raising the temperature of a portion that is not to be heat-treated ("unheated portion", the left side in FIG. 2 (B)) when heating the portion that is to be heated ("heated portion", the right side in FIG. 2 (B)). For example, the unheated portion should preferably be covered with a thermally insulating or heat-blocking member such as a towel or aluminum foil, or a screening material 10 should preferably be provided between the heated portion and the unheated portion. In the case in which the area between the scapulae and the waist on the back of a test subject is used as the aforementioned prescribed portion, the screening material 10 should preferably be arranged along the backbone of the test subject, though there is no limitation thereto.

The screening material 10, for example, screens heat (infrared rays) radiated from infrared lamps 20 in FIG. 2 (B), thereby preventing heat from reaching the unheated portion. The screening material 10 is preferably a material having low thermal conductivity. For example, a plate-shaped member composed of a foamed thermal insulation material such as urethane foam, or a fibrous thermal insulation material such as cork or cellulose fibers is preferably used.

The heating method is not particularly limited, and for example, irradiation with infrared light from infrared lamps 20 or the like is preferably used.

Additionally, during heat treatment, the temperature should preferably be checked by thermography; a thermometer or the like in order to confirm that the temperature of the heated portion is kept at a prescribed temperature. At the same time, the temperature of the unheated portion should also preferably be checked to be sure that it remains unchanged by thermography; a thermometer or the like.

The heat treatment is preferably implemented at a temperature higher than body surface temperature and not more than approximately 45° C. Body surface temperature can vary in accordance with the environmental temperature and the state of the test subject (whether or not the test subject has a fever, or whether before or after exercise). Preferably, a healthy person (not having a fever) is selected as the test subject, and the body surface temperature of a test subject who has been resting for a prescribed time (for example, 10 minutes, 30 minutes, 1 hour or the like) in an environment in which the temperature has been adjusted to an appropriate temperature (for example, 25° C.) is employed. Normally, the temperature should be approximately 30° C. or higher, and in some cases, may be 32° C. or higher, 35° C. or higher, or 37° C. or higher. The heat treatment should preferably be implemented at a temperature that is at least 1° C. or more, preferably 2° C. or more, and more preferably 3° C. or more higher than the body surface temperature. The upper limit of the heat treatment temperature should preferably be approximately 45° C. or lower, in consideration of the temperatures in which the cosmetic will actually be used (for example, the body surface temperature can be approximately 40° C., and in some cases, 41° C. to 45° C., under exposure to sunlight in the summertime), the safety of the test subject and the like.

In order to accurately evaluate the impact of heat, the heating time should preferably be at least 1 minute, and more preferably at least 10 minutes. The upper limit of the heating time is not particularly limited, but should normally be 60 minutes or less, and preferably 30 minutes or less.

After the heat treatment has ended, the heated portion is allowed to rest until the temperature falls and returns to normal skin temperature. Preferably, thermography, a thermometer or the like is used to check that the temperatures of the heated portion and the unheated portion have become about the same.

Next, after optionally removing the screening material 10 and the like, the ultraviolet protection effects (the absorbance etc.) of the sample coating films are measured (FIG. 2 (C)).

Specifically, sample-coated parts and uncoated parts near the sample-coated parts in the test portions are irradiated with ultraviolet rays, and after a prescribed time (normally 16 to 24 hours) elapses, the minimum dose of ultraviolet rays (MED) initially causing slight reddening with a clear boundary over an area that is at least two-thirds of an irradiated part is determined. The MED in the sample-coated parts is referred to as MEDp and the MED in the uncoated parts is referred to as MEDu. Using the MEDpi and MEDui determined for said test subject, the SPF (also referred to as SPFi) of the sample on the test subject is computed in accordance with the expression indicated below.

$$SPFi=(MEDpi)/(MEDui) \quad \text{[Mathematical Expression 1]}$$

The above steps are implemented for multiple test subjects, and the arithmetic mean (rounding off below the decimal point) value of the SPFi obtained for the respective text subjects is taken as the SPF of that sample.

In an evaluation method that is implemented in vivo, when PA measurement is employed as the ultraviolet protection effect measurement method, steps (i) and (ii) are implemented in the same manner as that described above, and instead of the SPF measurement in step (iii), the UVAPF or the PFA as measured in accordance with the Japanese Cosmetic Industry Association SPF Measurement Standards (as revised in 2011) or the ISO 24442 standard can be computed and displayed as a PA in accordance with the classification indicated below.

TABLE 1

| UVAPF | Classification |
| --- | --- |
| at least 2 and lower than 4 | PA+ |
| at least 4 and lower than 8 | PA++ |
| at least 8 and lower than 16 | PA+++ |
| at least 16 | PA++++ |

For in vivo measurements in which the skin of a test subject is irradiated with ultraviolet rays to compute the SPF and the UVAPF, it is preferable for the test subject to be shown an explanatory document in advance, to be well-informed of the purpose and the details regarding the measurements, and to obtain consent in writing.

Additionally, due to medical and ethical considerations, it is recommended that the test subject not expose the tested area (back area) to sunlight for a minimum of four weeks before the SPF measurements are taken.

Finally, in step (iv), changes in the ultraviolet protection effects due to heat can be detected by comparing the ultraviolet protection effects in the heated portions with the ultraviolet protection effects in the unheated portions.

The cosmetic according to the present invention can be obtained by selecting a sample composition in which the ultraviolet protection effects in the heated portions are higher than the ultraviolet protection effects in the unheated portions.

(B) In Vitro Evaluation Method

In the in vitro evaluation method, a resin substrate composed of PMMA, nylon, an acrylic plate or the like, or an inorganic matter plate composed of glass, silica or the like may be used as the substrate. Preferably, a skin substitute film (also called an "S plate", see JP 4453995 B) comprising a PMMA plate provided with V-shaped grooves on the surface or the like is used.

In step (i) illustrated in FIG. 1, a prescribed amount of a sample (sample composition) of the cosmetic is applied to a substrate surface and optionally dried to form a sample coating film.

Next, in step (ii), the substrate on which the sample coating film has been formed is heated. The heating method may be the above-mentioned infrared irradiation. However, the method may also be implemented by placing the substrate on which the sample coating film has been formed at rest in a thermostatic tank adjusted to a prescribed temperature. Alternatively, step (i) and step (ii) can be implemented at the same time by forming the sample coating film on a substrate that has been heated to the prescribed temperature beforehand.

The heating temperature should preferably be within the range from 30° C. to 70° C. If the heating temperature exceeds 70° C., then there are cases in which problems such as a substrate composed of resin melting or the like. As long as the temperature is within the aforementioned range, there are no particular limitations. For example, the heat treatment may be performed with the temperature at 32° C. or higher, 35° C. or higher, 37° C. or higher, or 40° C. or higher, and at 65° C. or lower, 60° C. or lower, 55° C. or lower, or 50° C. or lower.

The heating time is preferably at least 1 minute and more preferably at least 10 minutes in order to accurately evaluate the impact of heat. The upper limit of the heating time is not particularly limited, but should normally be 60 minutes or less, and preferably 30 minutes or less.

In the aforementioned step (i), it is preferable to form coating films with the same amount of the same sample on each of multiple substrates, to subject at least one (heated sample) of the coating films to the heat treatment in step (ii) and to keep the rest (unheated samples) at ambient temperature.

After step (ii) is completed, the substrate is preferably allowed to rest until the temperature returns to ambient temperature, and the absorbances, at prescribed wavelengths (in the UVA or UVA range), of the sample coating films on the respective substrates are measured (step (iii)).

The "absorbance measurement" in the present invention includes absorbance measurements at a single wavelength (ultraviolet range) and absorbance measurements across a prescribed wavelength range (including critical wavelength measurements).

The SPFs or the UVAPFs (or the PFAs) are computed based on the absorbances measured in step (iii), and may be used as indicators of the ultraviolet protection effects.

Next, in step (iv), changes in the ultraviolet protection effects due to heat can be detected by comparing the ultraviolet protection effects in the "heated samples" with the ultraviolet protection effects in the "unheated samples".

The cosmetic according to the present invention can be obtained by selecting a sample composition in which the ultraviolet protection effects in the heated portions are higher than the ultraviolet protection effects in the unheated portions.

Furthermore, by providing a step (i') for measuring the absorbances of the sample coating films formed in step (i), the change in the absorbances in the "heated samples" and the "unheated samples" in step (i) and step (iii) is made clear. Thus, by referring to these values, the change due to heat can be accurately determined by compensating for the change in the ultraviolet protection effects not caused by heat such as, for example, variations over time.

In the in vivo and in vitro measurements, the heat treatment (step (ii)) is preferably implemented in an environment from which ultraviolet rays are blocked for the purpose of eliminating the effects of factors other than heat.

2. Cosmetic

The cosmetic of the present invention can be obtained by the above-described manufacturing method.

Additionally, the cosmetic of the present invention contains the above-mentioned (A) ultraviolet protectant and the above-mentioned (B) humectant, and the absorbance of the coating film increases after the heat treatment.

The cosmetic of the present invention is selected by the above-described evaluation method or is such that the absorbance of the coating film increases after heat treatment. Thus, the ultraviolet protection effects conversely increase when heat is applied during actual use.

The cosmetic of the present invention may be in the form of an oil-based cosmetic, a water-in-oil emulsion cosmetic, an oil-in-water emulsion cosmetic, a multi-phase emulsion cosmetic or a water-based cosmetic, and is not particularly limited.

As the product form, the cosmetic may be provided not only as a sunscreen cosmetic, but also as a makeup base or a makeup cosmetic such as a foundation provided with sunscreen effects, a hair cosmetic (including various types of hair-care products such as hairsprays and hair treatments for protecting the hair or scalp from ultraviolet rays), a spray-type cosmetic or the like.

EXAMPLES

Hereinafter, the present invention will be explained in further detail by providing examples. However, the present invention is not limited to the examples below. Where not particularly indicated otherwise, the blended amounts are indicated in percentage by mass relative to the system in which the components in question are blended. (1) Water-in-oil emulsion cosmetic The water-in-oil emulsion cosmetic compositions indicated in Table 2 below were prepared. Specifically, after the powders were dispersed in the oil-based components mixed by using a homomixer, the well-mixed water-based components were added, thereby obtaining the compositions.

The resulting compositions were applied, in the application amount of 2 mg/cm², to PMMA plates at ambient temperature (25° C.), after which the absorbances at 280 to 400 nm were measured by using a spectrometer.

Samples of each example were dripped, in the amount of 2 mg/cm², onto S plates (5×5 cm V-groove PMMA plates, SPFMASTER-PA01), applied with a finger for 60 seconds, and dried for 15 minutes to form coating films. Using an uncoated plate as a control, the absorbances (280 to 400 nm) of the coating films were measured with a Hitachi U-3500 self-recording spectrophotometer, and the obtained measurement data was used to determine pre-heat treatment absorbance integral values.

Next, the measured plates were subjected to heat treatment for 30 minutes at 37° C. in isothermic tanks, and the post-heat treatment absorbance integral values were determined from the obtained measurement data.

The change (thermal reaction rate) in the absorbance integral values in the aforementioned wavelength range from before to after heating were computed in accordance with the following expression.

Thermal reaction rate (%)=(post-heat treatment absorbance integral value)/(pre-heat treatment absorbance integral value)×100

The values of the thermal reaction rates (%) of the respective samples are also indicated in Table 2.

TABLE 2

|  | Test Ex. 1 | Test Ex. 2 | Test Ex. 3 | Test Ex. 4 | Test Ex. 5 | Test Ex. 6 | Test Ex. 7 | Test Ex. 8 |
| --- | --- | --- | --- | --- | --- | --- | --- | --- |
| Water | bal | bal | bal | bal | bal | bal | bal | bal |
| Ethanol | 10 | 10 | 10 | 10 | 10 | 10 | 10 | 10 |
| Polyethylene glycol 300 | 10 | — | — | — | — | — | — | — |
| PEG/PPG-14/7 dimethyl ether | — | 10 | — | — | — | — | — | — |

TABLE 2-continued

|  | Test Ex. 1 | Test Ex. 2 | Test Ex. 3 | Test Ex. 4 | Test Ex. 5 | Test Ex. 6 | Test Ex. 7 | Test Ex. 8 |
|---|---|---|---|---|---|---|---|---|
| PEG/PPG-9/2 dimethyl ether | — | — | 10 | — | — | — | — | — |
| PEG/PPG-17/4 dimethyl ether | — | — | — | 10 | — | — | — | — |
| Polyethylene glycol 1500 | — | — | — | — | 10 | — | — | — |
| Polyethylene glycol 20000 | — | — | — | — | — | 10 | — | — |
| Glycerin | — | — | — | — | — | — | 10 | — |
| 1,3-Butylene glycol | — | — | — | — | — | — | — | 10 |
| Disteardimonium hectorite | 0.5 | 0.5 | 0.5 | 0.5 | 0.5 | 0.5 | 0.5 | 0.5 |
| PEG-9 polydimethylsiloxyethyl dimethicone | 2 | 2 | 2 | 2 | 2 | 2 | 2 | 2 |
| Diisopropyl sebacate | 5 | 5 | 5 | 10 | 10 | 10 | 5 | 5 |
| Dimethicone | 20 | 20 | 20 | 20 | 20 | 20 | 20 | 20 |
| Octocrylene | 5 | 5 | 5 | 5 | 5 | 5 | 5 | 5 |
| bis-Ethylhexyloxyphenol methoxyphenyl triazine | 1 | 1 | 1 | 1 | 1 | 1 | 1 | 1 |
| Diethylamino hydroxybenzoyl hexyl benzoate | 1 | 1 | 1 | 1 | 1 | 1 | 1 | 1 |
| Ethylhexyl triazone | 1 | 1 | 1 | 1 | 1 | 1 | 1 | 1 |
| Ethylhexyl methoxycinnamate | 5 | 5 | 5 | 5 | 5 | 5 | 5 | 5 |
| Hydrophobically treated fine-particle titanium oxide | 2 | 2 | 2 | 2 | 2 | 2 | 2 | 2 |
| Hydrophobically treated fine-particle zinc oxide | 10 | 10 | 10 | 10 | 10 | 10 | 10 | 10 |
| Spherical silicone rubber powder | 2 | 2 | 2 | 2 | 2 | 2 | 2 | 2 |
| Hydrophobically treated talc | 2 | 2 | 2 | 2 | 2 | 2 | 2 | 2 |
| Spherical crosslinked PMMA powder | 2 | 2 | 2 | 2 | 2 | 2 | 2 | 2 |
| Spherical silica | 2 | 2 | 2 | 2 | 2 | 2 | 2 | 2 |
| Chelating agent | s.a. | s.a | s.a. | s.a. | s.a. | s.a. | s.a. | s.a. |
| Total | 100 | 100 | 100 | 100 | 100 | 100 | 100 | 100 |
| Thermal reaction rate (%) | 111 | 108 | 117 | 108 | 109 | 108 | 100 | 101 |

As shown in Table 2, by blending prescribed humectants, an increase in the ultraviolet protection effects by heating was observed. However, said effect was not observed in the case in which glycerin (IOB=6.0), which has an IOB that is too high, was used as the humectant. Additionally, for both alkylene oxide derivatives and polyhydric alcohols, a tendency for the ultraviolet protection effects due to heat to become greater as the molecular weights became lower was observed.

(2) Oil-Based Cosmetic

The oil-based cosmetic compositions indicated in Table 3 below were prepared. Specifically, compositions were obtained by using a homomixer to mix the oil-based components with the humectant components. The values of the thermal reaction rates (%) of the samples are also indicated in Table 3.

TABLE 3

|  | Test Ex. 9 | Test Ex. 10 | Test Ex. 11 | Test Ex. 12 | Test Ex. 13 | Test Ex. 14 |
|---|---|---|---|---|---|---|
| Ethanol | bal | bal | bal | bal | bal | bal |
| PEG/PPG-9/2 dimethyl ether | 20 | — | — | — | — | — |
| PEG/PPG-14/7 dimethyl ether | — | 20 | — | — | — | — |
| Polyethylene glycol 300 | — | — | 20 | — | — | — |
| Polyethylene glycol 1500 | — | — | — | 20 | — | — |
| Glycerin | — | — | — | — | 20 | — |
| Ethylhexyl methoxycinnamate | 5 | 5 | 5 | 5 | 5 | 5 |
| 4-tert-Butyl-4'-methoxybenzoyl methane | 3 | 3 | 3 | 3 | 3 | 3 |
| Octyl salicylate | 5 | 5 | 5 | 5 | 5 | 5 |
| bis-Ethylhexyloxyphenol methoxyphenyl triazine | 2 | 2 | 2 | 2 | 2 | 2 |
| Octocrylene | 5 | 5 | 5 | 5 | 5 | 5 |
| Diethylamino hydroxybenzoyl hexyl benzoate | 2 | 2 | 2 | 2 | 2 | 2 |
| Diisopropyl sebacate | 5 | 5 | 5 | 5 | 5 | 5 |
| Total | 100 | 100 | 100 | 100 | 100 | 100 |
| Thermal reaction rate (%) | 145 | 109 | 132 | 123 | 83 | 100 |

As shown in Table 3, it was confirmed that the ultraviolet protection effects were increased by heating even in oil-based cosmetics.

(3) Oil-Based Cosmetics

All of the components indicated in Table 4 below were mixed by using a homomixer to obtain oil-based sunscreen cosmetics. In the case in which an oil solidifier was included, the oil solidifier was added to the oil-based components, then heated and melted, and after adding the humectant, mixed and homogenized, and thereafter cooled to obtain an oil-based solid sunscreen cosmetic. The values of the thermal reaction rates (%) of the respective samples are also indicated in Table 4.

TABLE 4

|  | Test Ex. 15 | Test Ex. 16 | Test Ex. 17 | Test Ex. 18 | Test Ex. 19 | Test Ex. 20 | Test Ex. 21 |
|---|---|---|---|---|---|---|---|
| Diisopropyl sebacate | bal | bal | bal | bal | bal | bal | bal |
| PEG/PPG-9/2 dimethyl ether | — | — | 15 | 15 | 15 | 15 | 15 |
| Ethylhexyl methoxycinnamate | 10 | 10 | 10 | 10 | 10 | 10 | 10 |
| 4-tert-Butyl-4'-methoxybenzoyl methane | 3 | 3 | 3 | 3 | 3 | 3 | 3 |
| Homosalate | 10 | 10 | 10 | 10 | 10 | 10 | 10 |
| bis-Ethylhexyloxyphenol methoxyphenyl triazine | 2 | 2 | 2 | 2 | 2 | 2 | 2 |
| Octocrylene | 5 | 5 | 5 | 5 | 5 | 5 | 5 |
| Diethylamino hydroxybenzoyl hexyl benzoate | 3 | 3 | 3 | 3 | 3 | 3 | 3 |
| Hydrogenated polydecene | 20 | 20 | 20 | 20 | 20 | 20 | 20 |
| Diphenylsiloxy phenyl trimethicone | 2 | 2 | 2 | 2 | 2 | 2 | 2 |
| Hydroxystearic acid | — | 6 | — | 10 | — | — | 6 |
| Polyamide-8 | — | 2 | — | — | 10 | — | 2 |
| Dibutyl lauroyl glutamide | — | 2 | — | — | — | 5 | 2 |
| Total | 100 | 100 | 100 | 100 | 100 | 100 | 100 |
| Thermal reaction rate (%) | 97 | 98 | 120 | 104 | 117 | 110 | 103 |

As shown in Table 4, it was confirmed that the ultraviolet protection effects were increased by heating even in oil-based cosmetics.

(4) Oil-In-Water Emulsion Cosmetic

The oil-in-water emulsion cosmetic composition indicated in Table 5 below was prepared. Specifically, after dispersing the powders in the oil-based components mixed by using a homomixer, the well-mixed water-based components were added to obtain the compositions. The value of the thermal reaction rate (%) of the sample is also indicated in Table 5.

TABLE 5

|  | Test Ex. 22 |
|---|---|
| Water | bal |
| Glycerin | 4 |
| 1,3-Butylene glycol | 7 |
| PEG/PPG-9/2 dimethyl ether | 5 |
| Succinoglycan | 0.12 |
| (Dimethylacrylamide/sodium acryloyldimethyl taurate) cross-polymer | 0.6 |
| PEG-60 hydrogenated castor oil | 1.6 |
| Diisopropyl sebacate | 4 |
| Non-volatile dimethicone | 2 |
| PPG-17 | 1 |
| Cyclomethicone | 12 |
| Triethylhexanoin | 5 |
| Isostearic acid | 1 |
| Sorbitan sesquiisostearate | 0.5 |
| Hydrophobically treated fine-particle zinc oxide | 10 |
| Ethylhexyl methoxycinnamate | 7 |
| Diethylamino hydroxybenzoyl hexyl benzoate | 1 |
| bis-Ethylhexyloxyphenol methoxyphenyl triazine | 2 |

TABLE 5-continued

|  | Test Ex. 22 |
|---|---|
| Spherical urethane resin powder | 1 |
| pH adjuster | s.a. |
| Chelating agent | s.a. |
| Preservative | s.a. |
| Total | 100 |
| Thermal reaction rate (%) | 106 |

As shown in Table 5, it was confirmed that the ultraviolet protection effects were increased by heating even in cosmetics that are in oil-in-water emulsion form.

(5) Water-In-Oil Emulsion Cosmetic

The water-in-oil emulsion cosmetic compositions indicated in Table 6 below were prepared. Specifically, after dispersing the powders in the oil-based components mixed by using a homomixer, the well-mixed water-based components were added to obtain the compositions. The values of the thermal reaction rates (%) of the samples are also indicated in Table 6.

TABLE 6

|  | Test Ex. 23 | Test Ex. 24 | Test Ex. 25 |
|---|---|---|---|
| Water | bal | bal | bal |
| Ethanol | 10 | 10 | 10 |
| Glycerin | 1 | 1 | 1 |
| Polyethylene glycol 300 | 10 | 10 | 10 |
| Disteardimonium hectorite | 0.5 | 0.5 | 0.5 |
| PEG-9 polydimethylsiloxyethyl dimethicone | 2 | 2 | 2 |
| Isostearic acid | 0.5 | 0.5 | 0.5 |
| Diisopropyl sebacate | 10 | 10 | 10 |
| Dimethicone | 20 | 20 | 20 |
| Octocrylene | 5 | 5 | 5 |
| bis-Ethylhexyloxyphenol methoxyphenyl triazine | 1 | 1 | 1 |
| Diethylamino hydroxybenzoyl hexyl benzoate | 1 | 1 | 1 |
| Ethylhexyl triazone | 1 | 1 | 1 |
| Ethylhexyl methoxycinnamate | 5 | 5 | 5 |

TABLE 6-continued

|  | Test Ex. 23 | Test Ex. 24 | Test Ex. 25 |
|---|---|---|---|
| 4-tert-Butyl-4'-methoxybenzoyl methane | 0.5 | 1 | 3 |
| Hydrophobically treated fine-particle titanium oxide | 2 | 2 | 2 |
| Hydrophobically treated fine-particle zinc oxide | 10 | 10 | 10 |
| Chelating agent | s.a. | s.a | s.a. |
| Total | 100 | 100 | 100 |
| Thermal reaction rate (%) | 111 | 107 | 103 |

As shown in Table 6, it was confirmed that, in the case in which t-butyl methoxy dibenzoyl methane was used as the (A) ultraviolet protectant, a higher thermal reaction rate was obtained when the blended amount thereof was smaller.

(6) Water-In-Oil Emulsion Cosmetic

The water-in-oil emulsion cosmetic compositions indicated in Table 7 below were prepared. Specifically, after dispersing the powders in the oil-based components mixed by using a homomixer, the well-mixed water-based components were added to obtain the compositions. The values of the thermal reaction rates (%) of the samples are also indicated in Table 7.

TABLE 7

|  | Test Ex. 26 | Test Ex. 27 | Test Ex. 28 | Test Ex. 29 | Test Ex. 30 | Test Ex. 31 |
|---|---|---|---|---|---|---|
| Water | bal | bal | bal | bal | bal | bal |
| Ethanol | 10 | 10 | 10 | 10 | 10 | 10 |
| Glycerin | 1 | 1 | 1 | 1 | 1 | 1 |
| PEG/PPG-9/2 dimethyl ether | — | 5 | 5 | 5 | 5 | 5 |
| Polyethylene glycol 300 | — | — | 5 | — | — | — |
| Polyethylene glycol 400 | — | — | — | 5 | — | — |
| Polyethylene glycol 1500 | — | — | — | — | 5 | — |
| Polyethylene glycol 20000 | — | — | — | — | — | 5 |
| Disteardimonium hectorite | 0.5 | 0.5 | 0.5 | 0.5 | 0.5 | 0.5 |
| Dextrin palmitate | 1 | 1 | 1 | 1 | 1 | 1 |
| PEG-9 polydimethylsiloxyethyl dimethicone | 2 | 2 | 2 | 2 | 2 | 2 |
| Isostearic acid | 1 | 1 | 1 | 1 | 1 | 1 |
| Diisopropyl sebacate | 5 | 5 | 5 | 5 | 5 | 5 |
| Cyclomethicone | 5 | 5 | 5 | 5 | 5 | 5 |
| Volatile dimethicone | 15 | 10 | 5 | 5 | 5 | 5 |
| Non-volatile dimethicone | 3 | 3 | 3 | 3 | 3 | 3 |
| Isododecane | 5 | 5 | 5 | 5 | 5 | 5 |
| Octocrylene | 4 | 4 | 4 | 4 | 4 | 4 |
| bis-Ethylhexyloxyphenol methoxyphenyl triazine | 1 | 1 | 1 | 1 | 1 | 1 |
| Diethylamino hydroxybenzoyl hexyl benzoate | 1 | 1 | 1 | 1 | 1 | 1 |
| Ethylhexyl triazone | 6 | 6 | 6 | 6 | 6 | 6 |
| Hydrophobically treated fine-particle titanium oxide | 4 | 4 | 4 | 4 | 4 | 4 |
| Hydrophobically treated fine-particle zinc oxide | 10 | 10 | 10 | 10 | 10 | 10 |
| Spherical silicone rubber powder | 3 | 3 | 3 | 3 | 3 | 3 |
| Hydrophobically treated talc | 3 | 3 | 3 | 3 | 3 | 3 |
| Spherical crosslinked PMMA powder | 3 | 3 | 3 | 3 | 3 | 3 |
| Spherical silica | 3 | 3 | 3 | 3 | 3 | 3 |
| Chelating agent | s.a. | s.a | s.a. | s.a. | s.a. | s.a. |
| Total | 100 | 100 | 100 | 100 | 100 | 100 |
| Thermal reaction rate (%) | 98 | 129 | 140 | 135 | 131 | 124 |

As shown in Table 7, the ultraviolet protection effect increase due to heat was prominent in the case in which both an alkylene oxide derivative and a polyhydric alcohol were used as the (B) humectant. In particular, extremely high effects were obtained by combining PEG/PPG-9/2 dimethyl ether and polyethylene glycol 300.

Hereinafter, examples of formulations of the cosmetic of the present invention will be indicated. Needless to say, the present invention is not limited in any way by these formulation examples, and is as defined by the claims. The blended amounts are all indicated in percentage by mass relative to the total amount of the cosmetic.

Formulation Example 1: Water-in-oil sunscreen
(Component name) Blended amount (% by mass)
Water balance
Ethanol 10
Polyethylene glycol 400 10
Disteardimonium hectorite 0.5
PEG-9 polydimethylsiloxyethyl dimethicone 2
Diisopropyl sebacate 5
Dimethicone 20
Octocrylene 5
bis-Ethylhexyloxyphenol methoxyphenyl triazine 1
Diethylamino hydroxybenzoyl hexyl benzoate 1
Ethylhexyl triazone 1
Ethylhexyl methoxycinnamate 5
Hydrophobically treated fine-particle titanium oxide 2
Hydrophobically treated fine-particle zinc oxide 10
Spherical silicone rubber powder 2
Hydrophobically treated talc 2
Spherical crosslinked PMMA powder 2
Spherical silica 2
Chelating agent s.a.

Formulation example 2: Two-layer makeup base
(Component name) Blended amount (% by mass)
Purified water balance
Ethanol 5
PEG/PPG-9/2 dimethyl ether 5
Glycerin 1
Xylitol 1

Potentilla erecta extract 0.3
Sodium hyaluronate 0.1
2-O-ethyl-L-ascorbic acid 0.1
Dipotassium glycyrrhizinate 0.05
Isododecane 3
Diisopropyl sebacate 10
PBG/PPG-9/1 copolymer 1
Dimethicone 13
Caprylyl methicone 3
Highly polymerized aminopropyl dimethicone 20% dimethicone solution 1
Trifluoroalkyl dimethyl trimethyl siloxysilicic acid 50% dimethicone solution 3
Dextrin palmitate 0.5
Ethylhexyl methoxycinnamate 7
Octocrylene 5
Diethylamino hydroxybenzoyl hexyl benzoate 1
bis-Ethylhexyloxyphenol methoxyphenyl triazine 0.5
Hydrophobic fine-particle titanium oxide 2
Hydrophobically treated fine-particle zinc oxide 5
Hydrophobically treated pigment-grade titanium oxide 1
Hydrophobically treated iron oxide 0.07
Methyl methacrylate cross-polymer 2
(Vinyl dimethicone/methicone silsesquioxane) cross-polymer 2
Hydrophobically treated talc 2
PEG-9 polydimethyl polysiloyethyl dimethicone 1.5
PEG/PPG-19/19 dimethicone 0.3
Dimethyl distearyl ammonium hectorite 0.4
Isostearic acid 0.3
EDTA·3Na s.a.
Table salt s.a.
Sodium pyrosulfite s.a.
Tocopherol s.a.
Fragrance s.a.
Formulation example 3: Cream-type foundation cream
(Component name) Blended amount (% by mass)
Purified water balance
Ethanol 5
Phenoxyethanol 1
PEG/PPG-9/2 dimethyl ether 5
Glycerin 3
Erythritol 1
Xylitol 1
Potentilla erecta extract 1
Glycylglycine 0.1
Tranexamic acid 1
Dipotassium glycyrrhizinate 0.05
Tripropylene glycol pivalate 2
Diisopropyl sebacate 5
Dimethicone 10
Cyclomethicone 5
Trisiloxysilicic acid 50% cyclopentasiloxane solution 2
Dextrin palmitate 1
Ethylhexyl methoxycinnamate 7
Hydrophobic fine-particle titanium oxide 3
Hydrophobic fine-particle zinc oxide 3
Hydrophobically treated pigment-grade titanium oxide 6
Hydrophobically treated iron oxide 3.2
Hydrophobically treated barium sulfate-coated titanated mica 0.01
Hydrophobically treated titanated mica 0.01
Dimethicone cross-polymer 13% cyclopentasiloxane mixture 2
Polymethyl silsesquioxane 2
Methyl methacrylate cross-polymer 2
Hydrophobic fine-particle silica 0.5
Lauryl PEG-9 polydimethyl polysiloxyethyl dimethicone 2
(Dimethicone/(PEG-10/15)) cross-polymer 1
Dimethyl distearyl ammonium hectorite 1
Isostearic acid 0.2
Tocopherol s.a.
EDTA.3Na s.a.
Table salt s.a.
Sodium pyrosulfite s.a.
Fragrance s.a.
Formulation example 4: Aerosol spray-type sunscreen
(Component name) Blended amount (% by mass)
Purified water balance
Ethanol 5
Polyethylene glycol 300 2
Silica 0.5
Glycerin 1
PEG/PPG-14/7 dimethyl ether 6
DL-a-tocopherol acetate 0.5
D-glutamic acid 0.1
Stearyl glycyrrhizinate 0.1
Isododecane 10
Glyceryl tri-2-ethylhexanoate 5
Isopropyl myristate 3
Diisopropyl sebacate 5
PBG/PPG-9/1 copolymer 1
Dimethicone 13
Trisiloxysilicic acid 50% cyclopentasiloxane solution 0.5
Sucrose tetrastearate triacetate 0.5
Dextrin palmitate 1
Ethylhexyl methoxycinnamate 5
Diethylamino hydroxybenzoyl hexyl benzoate 2
bis-Ethylhexyloxyphenol methoxyphenyl triazine 1
Polysilicone-15 2
Octocrylene 5
Methyl methacrylate cross-polymer 5
(Vinyl dimethicone/methicone silsesquioxane) cross-polymer 3
Hydrophobically treated talc 1
Cetyl PEG/PPG-10/1 dimethicone 1
Lauryl PEG-9 polydimethyl polysiloxyethyl dimethicone 1
Dimethyl distearyl ammonium hectorite 0.5
Isostearic acid 0.3
Sorbitan sequiisostearate 0.3
EDTA.3Na s.a.
Tocopherol s.a.
Fragrance s.a.
The above-mentioned components were mixed to form a stock solution, and a spray can was filled with the stock solution and LPG at a ratio of 50:50 to obtain an aerosol spray-type sunscreen.
Formulation example 5: Gel-type BB cream
(Component name) Blended amount (% by mass)
Purified water balance
Ethanol 8
PEG/PPG-9/2 dimethyl ether 5
Rosa roxburghii extract 0.1
Stearoxyhydroxypropylmethylcellulose 0.2
(Dimethylacrylamide/sodium acryloyldimethyl taurate) copolymer 0.2
Succinoglucan 0.1
Glycerin 3
Polyethylene glycol 300 1
bis-PEG-18 methyl ether dimethyl silane 3
PEG/PPG-14/7 dimethyl ether 1
Ethylhexyl methoxycinnamate 10

Diisopropyl sebacate 5
Diethylamino hydroxybenzoyl hexyl benzoate 1
bis-Ethylhexyloxyphenol methoxyphenyl triazine 3
Hydrophobic fine-particle titanium oxide 3
Hydrophobically treated fine-particle zinc oxide 5
Hydrophobically treated pigment-grade titanium 4
Hydrophobically treated iron oxide 0.4
Isopropyl myristate 2
Polypropylene glycol (17) 2
Di (cholesteryl/phytosteryl)N-lauroyl-L-glutamate 0.5
Dextrin (palmitate/ethylhexanoate) 0.5
Fragrance s.a.
Silica 1
Formulation example 6: Milky lotion-cream type BB cream
(Component name) Blended amount (% by mass)
Purified water balance
Ethanol 6
Magnesium L-ascorbyl phosphate 0.5
Acetylated sodium hyaluronate 0.1
Water-soluble collagen 0.1
*Rosa roxburghii* extract 0.1
(Dimethylacrylamide/sodium acryloyldimethyl taurate) copolymer 0.3
Succinoglucan 0.2
Cellulose gum 0.2
Glycerin 2
Butylene glycol 4
PEG/PPG-14/7 dimethyl ether 3
PEG/PPG-9/2 dimethyl ether 2
Polyethylene glycol 300 1
Polyoxyethylene hardened castor oil (100 mole) 1
Polyoxyethylene (8 mole) behenyl ether 1
Sodium stearoyl methyltaurate 0.1
Stearyl alcohol 0.5
Behenyl alcohol 0.5
Ethylhexyl methoxycinnamate 8
Octocrylene 2
Ethylhexyl triazine 1
Diethylamino hydroxybenzoyl hexyl benzoate 1
bis-Ethylhexyloxyphenol methoxyphenyl triazine 1
Isododecane 10
Diisopropyl sebacate 5
Dimethicone 2
Phytosteryl macadamiate 1
Di (phytosteryl/octyldodecyl)N-lauroyl-L-glutamate 0.5
Dextrin (palmitate/ethylhexanoate) 0.5
Hydrophobically treated fine-particle zinc oxide 8
Pigment-grade hydrophobically treated titanium oxide 4
Hydrophobically treated iron oxide 0.2
Isostearic acid 0.5
Sorbitan sesquiisostearate 0.5
EDTA-2Na.H2O s.a.
Sodium hexametaphosphate s.a.
Citric acid s.a.
Sodium citrate s.a.
Fragrance s.a.
Talc 3
Silica 3

DESCRIPTION OF REFERENCE SYMBOLS

1 Sample
2 Substrate
10 Screening material
20 Infrared lamp

The invention claimed is:

1. A manufacturing method for a cosmetic in which ultraviolet protection effects are increased by heat, the method including
   (1) a step of preparing a sample composition containing (A) an ultraviolet protectant and (B) one or more humectants that have an IOB (Inorganic/Organic Balance) of 5.0 or lower and that are selected from among alkylene oxide derivatives and polyhydric alcohols; and
   (2) a step of selecting a sample composition in which ultraviolet protection effects are increased after heat treatment in comparison to before heat treatment, in accordance with an evaluation method including the following steps (i) to (iv):
      (i) a step of forming a coating film of the sample composition on a substrate,
      (ii) a step of heat-treating the coating film of the sample composition,
      (iii) a step of measuring ultraviolet protection effects of the coating film of the sample composition that has not been heat-treated and of the coating film of the sample composition that has been heat-treated, and
      (iv) a step of comparing the measured ultraviolet protection effects.

2. The manufacturing method as in claim 1, wherein the (B) one or more humectants are
   a polyoxyalkylene/polyoxyethylene copolymer dialkyl ether represented by the following formula (I):

$$R_1O\text{-}[(AO)_m(EO)_n]\text{-}R_2 \qquad (I)$$

wherein AO denotes an oxyalkylene group having three or four carbon atoms, EO denotes an oxyethylene group, $R_1$ and $R_2$, each independently, denote a hydrogen atom or a hydrocarbon group having one to four carbon atoms, $1 \le m \le 70$ and $1 \le n \le 70$;
   a polyhydric alcohol selected from the group consisting of polyalkylene glycols represented by the following formula (II):

$$HO(RO)_pH \qquad (II)$$

wherein RO denotes an oxyalkylene group having two to four carbon atoms and p is 3 to 500, and butylene glycol, dipropylene glycol, diglycerin, propanediol, erythritol, xylitol, methylglyceth-10 and sorbitol; or
   a combination thereof.

3. The manufacturing method as in claim 2, wherein the (B) one or more humectants are PEG/PPG-9/2 dimethyl ether and polyethylene glycol 300.

4. The manufacturing method as in claim 1, wherein when the ultraviolet protectant contains 4-tert-butyl-4'-methoxydibenzoyl methane, an amount of 4-tert-butyl-4'-methoxydibenzoyl methane is less than 0.5% by mass relative to the total amount of the cosmetic.

5. The manufacturing method as in claim 1, wherein the evaluation method is implemented in vivo.

6. The manufacturing method as in claim 1, wherein the evaluation method is implemented in vitro.

\* \* \* \* \*